United States Patent [19]
Amplatz et al.

[11] Patent Number: 5,607,419
[45] Date of Patent: Mar. 4, 1997

[54] METHOD AND APPARATUS FOR TREATING VESSEL WALL WITH UV RADIATION FOLLOWING ANGIOPLASTY

[75] Inventors: Curtis A. Amplatz, St. Paul; James S. Sharrow, Bloomington, both of Minn.

[73] Assignee: AngioMedics II Inc., Plymouth, Minn.

[21] Appl. No.: 426,855

[22] Filed: Apr. 24, 1995

[51] Int. Cl.⁶ ........................................ A61B 17/36
[52] U.S. Cl. ............................ 606/7; 606/15; 606/17
[58] Field of Search .......................... 606/7, 9, 10, 11, 606/12, 13, 14, 15, 16, 17, 18

[56] References Cited

U.S. PATENT DOCUMENTS

| | | |
|---|---|---|
| Re. 34,544 | 2/1994 | Spears . |
| Re. 34,695 | 8/1994 | Mar et al. . |
| 4,336,809 | 6/1982 | Clark . |
| 4,470,407 | 9/1984 | Hussein . |
| 4,512,762 | 4/1985 | Spears . |
| 4,660,925 | 4/1987 | McCaughan, Jr. . |
| 4,862,886 | 9/1989 | Clarke et al. . |
| 5,053,033 | 10/1991 | Clarke . |
| 5,163,935 | 11/1992 | Black et al. ............... 606/17 |
| 5,169,395 | 12/1992 | Narcisco, Jr. . |
| 5,196,005 | 3/1993 | Doiron et al. . |
| 5,207,669 | 5/1993 | Baker et al. . |
| 5,242,438 | 9/1993 | Saadatmanesh et al. ............... 606/15 |
| 5,330,465 | 7/1994 | Doiron et al. ............... 606/16 |
| 5,496,309 | 3/1996 | Saadat et al. ............... 606/15 |
| 5,514,128 | 5/1996 | Hillsman et al. ............... 606/7 |

*Primary Examiner*—Angela D. Sykes
*Assistant Examiner*—Sonya Harris-Ogugua
*Attorney, Agent, or Firm*—Haugen and Nikolai, P.A.

[57] ABSTRACT

Disclosed is an apparatus for use in applying UV light to a blood vessel wall following the performance of a balloon angioplasty procedure. It comprises an elongated optical fiber whose outside diameter permits it to be inserted into the lumen of a guidewire that is used to position the angioplasty balloon at the site of the lesion to be treated. The guidewire is provided with a light port and a suitable reflector is provided for causing UV light transmitted through the optical fiber to be radiated in a radial direction through the light port in the guidewire to thereby irradiate the vessel wall with UV energy that has been found effective in retarding growth of smooth muscle cells.

11 Claims, 1 Drawing Sheet

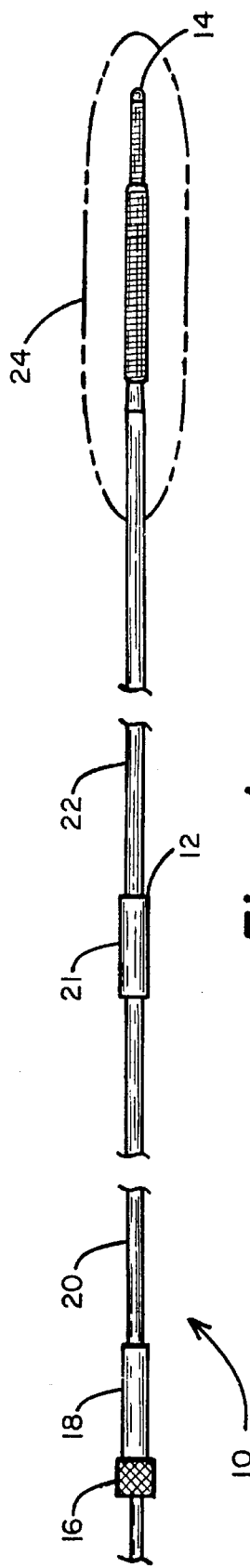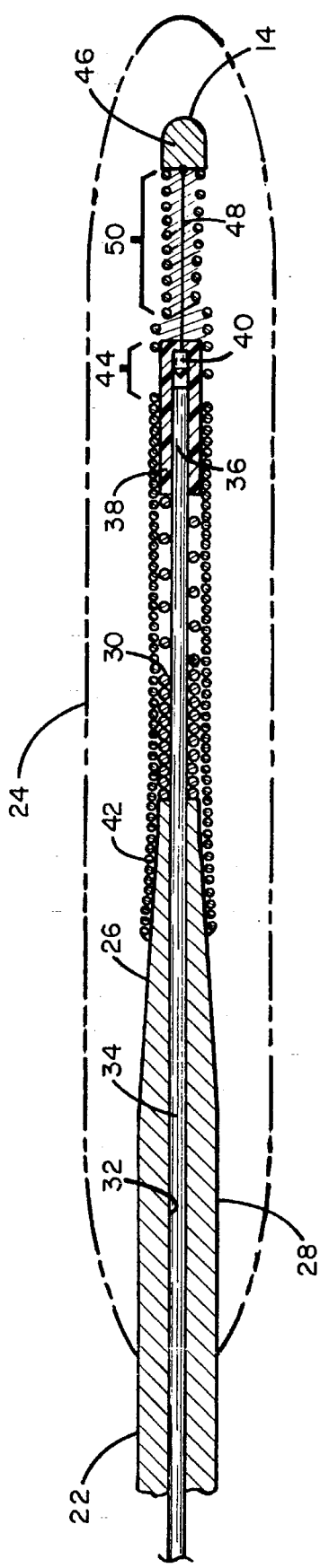

ns of the invention are achieved by providing a light diffusing optical waveguide assembly that comprises an elongated optical fiber having a longitudinal axis, a proximal end and a distal end, there being a connector affixed to the proximal end for coupling the optical fiber to a source of coherent light of a predetermined frequency, e.g., UV light in the 240 nm to 280 nm range. A light deflector is disposed proximate the distal end of the optical fiber and held in place by a tubular sleeve that is substantially transparent to the light being transmitted such that the light exiting the distal end of the light fiber is
METHOD AND APPARATUS FOR TREATING VESSEL WALL WITH UV RADIATION FOLLOWING ANGIOPLASTY

BACKGROUND OF THE INVENTION

I. Field of the Invention

This invention relates generally to apparatus for treating stenotic lesions on the interior walls of blood vessels, and more particularly to a device useable during a balloon angioplasty procedure for treating the site so as to reduce the incidences of restenosis.

II. Discussion of the Prior Art

In the Clarke et al. U.S. Pat. No. 5,053,033, there is described a method and apparatus for reducing the proliferation of smooth muscle cells in the blood vessel walls at an angioplasty site by irradiating it with UV radiation. In accordance with the teachings of the Clarke et al. patent, the UV radiation is delivered to the angioplasty site by way of an optical fiber or other waveguide incorporated into a percutaneous catheter, which is preferably a balloon angioplasty catheter having a lumen through which the laser fiber is inserted, After the balloon has been inflated to increase the lumenal diameter of the vessel, the balloon is deflated and the catheter backed off a short distance in the proximal direction so as to position the distal end of the optical fiber at a location so that UV light transmitted through the optical fiber and emanating from its distal end will impinge upon the angioplasty treatment site, Reissue U.S. Pat. No. 34,544 to Spears also describes a method for treatment of an artery or other blood vessel containing etherosclerotic plaque in which a drug, hematoporphyrin, is injected and absorbed into the plaque. Subsequently, the site is illuminated from an external light source connected to the proximal end of an optical waveguide. A light diffusing device coupled to the distal end of the waveguide and contained within the balloon itself disperses the light uniformly over a portion of the area occupied by the balloon.

Optical fibers, by their very nature, are brittle and small in diameter, have very poor flexural modulus, column strength and torqueability. This makes it difficult to pass them through a lumen, such as a guidewire lumen, of a conventional balloon angioplasty catheter.

It is accordingly a principal object of the present invention to provide a new and improved device for applying UV radiation to the site of a stenotic lesion that has been opened by an interventional technique such as in a balloon angioplasty procedure.

Another object of the invention is to provide a light emitting device that may be readily passed down the guidewire lumen of a conventional balloon catheter.

SUMMARY OF THE INVENTION

The foregoing objects and advantages of the present invention are achieved by providing a light diffusing optical waveguide assembly that comprises an elongated optical fiber having a longitudinal axis, a proximal end and a distal end, there being a connector affixed to the proximal end for coupling the optical fiber to a source of coherent light of a predetermined frequency, e.g., UV light in the 240 nm to 280 nm range. A light deflector is disposed proximate the distal end of the optical fiber and held in place by a tubular sleeve that is substantially transparent to the light being transmitted such that the light exiting the distal end of the light fiber is directed at a predetermined angle, e.g., 90 degrees to the longitudinal axis of the optical fiber.

The optical fiber with its attached light deflector is designed to fit within a lumen of a guidewire of the type used with balloon angioplasty catheters. Such a guidewire includes an elongated, flexible, tubular metal shaft member having a proximal end, a distal end and a lumen extending therebetween. The tubular metal shaft member has an outer diameter sufficiently small to fit through the working lumen of an intravascular catheter. Affixed to the distal end of the shaft member is a helically wound metal wire coil having a closed convolution section extending beyond the distal end of the flexible tubular metal shaft member. The closed convolution section is interrupted by an open convolution section that is intermediate the closed convolutions section.

The optical fiber with its attached light deflector is inserted through the lumen of the tubular metal shaft member comprising the guidewire assembly until the light deflector portion thereof is disposed in the open convolution section. Thus, light energy transmitted through the optical fiber is deflected radially outward and passes between the spaced-apart convolutions of the helically wound metal wire coil in the open convolution section. This guidewire assembly is insertable through the guidewire lumen of conventional balloon catheters and affords torqueability and pushability to the optical fiber.

DESCRIPTION OF THE DRAWINGS

FIG. 1 is an elevation view of a light emitting guidewire in accordance with the present invention; and FIG. 2 is a greatly exploded, cross-sectional view of the distal end portion of the light emitting guidewire of FIG. 1.

DESCRIPTION OF THE PREFERRED EMBODIMENT

Referring first to FIG. 1, there is indicated generally by numeral 10 a guidewire assembly incorporating a light diffusing optical waveguide comprising a preferred embodiment of the present invention. The guidewire assembly has a proximal end 12 and a distal end 14. Affixed to the proximal end 12 is an optical connector 16 capable of mating the guidewire assembly to a source of optical energy, such as a laser or a laser diode producing coherent UV light at a predetermined wavelength, preferably in the range of from 240 nm to 280 nm wavelength. A tubular strain relief member 18 joins the optical connector 16 to proximal end of an optical furcation cable 20 which, in turn, is secured to the proximal end 12 of the guidewire assembly by means of a suitable adhesive contained within a short length of heat shrink tubing 21. The major portion of the guidewire 10 comprises an elongated flexible tubular metal shaft member 22 which may, for example, comprise a 0.0165 O.D.×0.008 I.D. stainless steel tube that may typically be about 150 cm in length. The distal end portion shown enclosed by the broken line oval 24 is shown in greatly enlarged scale and is longitudinally cross-sectioned in the drawing of FIG. 2. The elongated, flexible tubular shaft member 22 has a uniform O.D. over substantially its entire length but is tapered over a short distal zone 26 to a lesser diameter.

The outer surface of the elongated flexible tubular shaft member 22 is preferably provided with a low friction coating over substantially its entire length. A suitable coating material is Teflon®, which renders that surface more lubricous and making the guidewire more readily passable through the guidewire lumen of an angioplasty catheter (not shown).

Soldered, brazed, or adhesive bound to the distal end of the elongated shaft member 22 is a short length of radiopaque wire, which is wound as a coil having an outer diameter of approximately 0.018 in. This inner wire coil is identified by numeral 30 and, as will be explained, functions as a strain relief to prevent sharp bending of the distal end portion of the optical guidewire assembly 10. Rather than a wire of circular cross-section, the coil 30 may be formed from a metal ribbon as well.

Extending through the lumen 32 of the elongated flexible tubular metal member 22 and through the center of the coiled wire strain relief member 30 is an optical fiber preferably formed from fused silica, the optical fiber being identified by numeral 34. The optical fiber 34 extends uninterrupted through the heat shrink 21, the optical furcation cable 20, and the optical connector 16.

Surrounding the distal end portion 36 of the optical fiber 34 is a short length of shrink tubing 38. It possesses the property of being substantially transparent to the UV light energy to be transmitted down the optical fiber 34. This shrink tubing functions to hold a light deflector 40 in a desired position relative to the distal end face of the optical fiber 34.

The light deflector 40 preferably comprises a polished metal cone whose apex is aligned with the longitudinal axis of the optical fiber 34. With a cone angle in the range of from 25 degrees to 50 degrees, light emanating generally longitudinally from the distal end 36 of the optical fiber 34 is deflected substantially perpendicularly to the longitudinal axis of the light fiber. While a polished metal cone preferably comprises the light deflector 40, an alternative light deflector may consist of a fused silica cone having a mirror coating thereon.

Also affixed by soldering or brazing to the outer surface of the elongated flexible metal tubular member 22 in the tapered zone 26 is a helically coiled wire 42, which may be stainless steel. It is coiled to create an outside diameter of approximately 0.0125 in. Adjacent convolutions of the helically coiled wire member 42 are closed relative to one another over substantially the entire length except for a short, intermediate section, defined by bracket 44, where the convolutions are stretched to an open configuration to define a radial light port. It is to be especially observed that the open convolutions are proximate the conically shaped light deflector 40. Thus, light traveling down the optical fiber 34 and exiting the distal face thereof impinge on the reflector 40 and are reflected out through the light port, i.e., the space between adjacent convolutions in the open segment 17 thereof.

A radiopaque tip member 46 is brazed onto the distal end of the stainless helically wound wire 42 and a safety wire 48 is deployed between the tip 46 and the deflector 44 to better secure the tip 46 to the remainder of the guidewire assembly.

It has also been found expedient to reduce the O.D. of the helically wound outer coil 42 in the zone identified by bracket 50 to improve the flexibility properties of the distal end portion of the light emitting guidewire assembly 10.

In use during the performance of a coronary angioplasty procedure, a guide catheter may be introduced into the patient using the conventional Seldinger technique, the guide catheter being advanced through the vascular system until its distal end is adjacent the coronary ostium. A balloon angioplasty catheter having the light emitting guidewire 10 of the present invention disposed in its guidewire lumen is then advanced through the guide catheter until the distal end of the balloon angioplasty catheter is also proximate the coronary ostium. At this point, the guidewire 10 is advanced until the distal tip 46 extends across the lesion to be treated in the effected coronary artery. Once the guidewire is so positioned, the balloon angioplasty catheter is also advanced over the guidewire until its balloon is disposed adjacent the stenotic lesion to be expanded. The surgeon then causes the balloon to be inflated by injecting a fluid through a lumen of the angioplasty catheter and out through a port spanned by the balloon. Once the stenotic lesion has been compressed into the vessel wall, the balloon can be deflated and the working catheter withdrawn sufficiently far so that the light port in zone 17 defined by the open convolutions in the coil wired segment 42 is disposed adjacent the treatment site. Next, UV light of a wavelength found to suppress the growth of smooth muscle cells is transmitted down the optical fiber 32 and, upon striking the light deflector 40, exits through the open convolutions in the guidewire distal end portion to bathe the walls of the blood vessel at the site of the lesion with UV light. Where the treatment site is longer than the width of the short band of light reflected through the spaced convolutions, it is necessary to sequentially treat the total site by repeated stepwise displacements of the guidewire.

To assure that the light exiting the guidewire is not occluded by blood, the balloon can be periodically inflated to block blood flow through the affected artery and a saline flush may be made to exit the working lumen of the angioplasty catheter. In accordance with the teachings of the aforereferenced Clarke '033 patent, bathing the site with UV light has been found to materially reduce incidences of restenosis following a balloon angioplasty procedure.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. For example, another method of use would be to replace the dilating balloon after a successful dilatation of the artery with a second balloon for administering the UV light via the light emitting guidewire of the present invention. The second balloon catheter would be made of materials that are transparent to UV light so that the light could be shined out through the balloon. The reflecting cone device 40 would reside inside the balloon during use. This method eliminates the need for perfusion, since the balloon itself will squeeze the blood out of the field, and expose the tissue to light. The light emitting device would need to be removed to several locations inside the UV light transparent balloon since it does not spread the light enough to fill the entire balloon at once. A second balloon is necessary since the dilatation balloon of the first catheter would typically be filled with contrast fluid, which cannot be penetrated by UV light. The balloon on the second catheter used for lighting the artery would be filled with saline.

What is claimed is:

1. A light diffusing optical waveguide assembly adapted to be inserted into a guidewire lumen of an intravascular catheter comprising:

(a) an elongated, flexible, tubular metal shaft member having a proximal end, a distal end and a lumen extending therebetween, the tubular metal shaft member having an outer diameter small enough to fit through a working lumen of an intravascular catheter;

(b) an optical fiber having a proximal end, a distal end and a longitudinal axis, said optical fiber having an outer diameter allowing it to fit through said lumen of said tubular metal shaft member and a light deflector affixed to the optical fiber in spaced relation to said distal end of said optical fiber said distal end of said optical fiber for deflecting light waves transmitted down said optical fiber at a predetermined angle to said longitudinal axis;

(c) a helically wound metal wire affixed to said shaft member at the distal end thereof, said helical wound metal wire having a closed convolutions section extending beyond said distal end of said shaft member and an open convolutions section intermediate said closed section and adjacent said deflector so that light waves deflected from said deflector at the predetermined angle is able to pass between the open convolutions of the helical wound wire in the intermediate open convolutions section.

2. The light diffusing optical waveguide assembly as in claim 1 wherein said light deflector comprises a cone-shaped reflector having an apex aligned with said longitudinal axis of said optical fiber.

3. The light diffusing optical waveguide assembly as in claim 2 wherein said cone-shaped reflector is made of a polished metal.

4. The light diffusing optical waveguide assembly as in claim 2 wherein said cone-shaped reflector is a fused silica having a metalized coating thereon.

5. The light diffusing optical waveguide assembly as in claim 1 and further including:

(a) an optical connector affixed to said proximal end of said optical fiber and the proximal end of said elongated flexible tubular metal member for coupling said optical fiber assembly to a source of ultraviolet radiation.

6. The light diffusing optical waveguide assembly as in claim 5 wherein said ultraviolet radiation has a wave length in the range of from 240 nm to 280 nm.

7. The light diffusing optical waveguide assembly as in claim 5 and further including a tubular sleeve for affixing said light deflector to said distal end of said optical fiber, said tubular sleeve being substantially transparent to ultraviolet radiation.

8. The light diffusing waveguide assembly as in claim 7 wherein said tubular sleeve is formed from Teflon®.

9. The light diffusing optical waveguide assembly as in claim 7 and further including a radiopaque tip member affixed to said helically wound metal wire and a safety wire extending between said tip member and said light deflector within said tubular sleeve.

10. The light diffusing optical waveguide assembly as in claim 1 and further including a low friction coating on said elongated, flexible, metal member.

11. The light diffusing optical waveguide assembly as in claim 2 wherein said cone-shaped reflector has a cone angle in the range of from 25 degrees to 50 degrees.

* * * * *